(12) United States Patent
Morton

(10) Patent No.: US 9,675,306 B2
(45) Date of Patent: *Jun. 13, 2017

(54) X-RAY SCANNING SYSTEM

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 14/460,073

(22) Filed: Aug. 14, 2014

(65) Prior Publication Data

US 2015/0043707 A1    Feb. 12, 2015

Related U.S. Application Data

(63) Continuation of application No. 13/304,738, filed on Nov. 28, 2011, now Pat. No. 8,837,669, which is a
(Continued)

(30) Foreign Application Priority Data

Apr. 25, 2003   (GB) .................................. 0309379.6

(51) Int. Cl.
*A61B 6/00* (2006.01)
*A61B 6/02* (2006.01)
(Continued)

(52) U.S. Cl.
CPC ............ *A61B 6/4028* (2013.01); *A61B 6/022* (2013.01); *A61B 6/027* (2013.01); *A61B 6/032* (2013.01);
(Continued)

(58) Field of Classification Search
CPC .......... A61B 6/00; A61B 6/02; A61B 6/4028; A61B 6/487; A61B 6/504; A61B 6/022; A61B 6/032; G03C 9/00; G03C 9/08
(Continued)

(56) References Cited

U.S. PATENT DOCUMENTS 2,299,251 A    10/1942   Perbal
2,831,123 A    4/1958    Daly
(Continued)

FOREIGN PATENT DOCUMENTS

AT           392160 B      2/1991
AU        2003254124 A1    2/2004
(Continued)

OTHER PUBLICATIONS

US 5,987,079, 11/1999, Scott (withdrawn)
(Continued)

*Primary Examiner* — Jurie Yun
(74) *Attorney, Agent, or Firm* — Novel IP

(57) ABSTRACT

This specification discloses methods and systems for generating a stereo image of an object that is positioned within an imaging volume. The object is positioned within the imaging volume. Two stationary X-ray source points are selected and activated. X-rays from both stationary X-ray source points are transmitted through the object being scanned and detected using detector elements positioned across the imaging volume and opposite the stationary X-ray source points. Image data sets from the X-rays detected by the detector elements are generated and then combined to produce the stereo image.

14 Claims, 4 Drawing Sheets

Related U.S. Application Data continuation of application No. 12/697,073, filed on Jan. 29, 2010, now Pat. No. 8,085,897, which is a continuation of application No. 10/554,570, filed as application No. PCT/GB2004/001747 on Apr. 23, 2004, now Pat. No. 7,684,538.

(51) Int. Cl.
 *A61B 6/03* (2006.01)
 *A61B 6/06* (2006.01)

(52) U.S. Cl.
 CPC ............... *A61B 6/06* (2013.01); *A61B 6/487* (2013.01); *A61B 6/504* (2013.01); *A61B 6/503* (2013.01)

(58) Field of Classification Search
 USPC ............ 378/4, 10, 12, 41, 42, 114, 115, 116
 See application file for complete search history.

(56) References Cited

U.S. PATENT DOCUMENTS

| | | | |
|---|---|---|---|
| 2,952,790 | A | 9/1960 | Steen |
| 2,999,935 | A | 9/1961 | Foster |
| 3,239,706 | A | 3/1966 | Farrell |
| 3,707,672 | A | 12/1972 | Miller |
| 3,713,156 | A | 1/1973 | Pothier |
| 3,766,387 | A | 10/1973 | Heffan |
| 3,768,645 | A | 10/1973 | Conway |
| 3,784,837 | A | 1/1974 | Holmstrom |
| 3,848,130 | A | 11/1974 | Macovski |
| 3,854,049 | A | 12/1974 | Mistretta |
| RE28,544 | E | 9/1975 | Stein |
| 3,965,358 | A | 6/1976 | Macovski |
| 3,980,889 | A | 9/1976 | Haas |
| 4,047,035 | A | 9/1977 | Dennhoven |
| 4,057,725 | A | 11/1977 | Wagner |
| 4,105,922 | A | 8/1978 | Lambert |
| 4,122,783 | A | 10/1978 | Pretini |
| 4,139,771 | A | 2/1979 | Dennhoven |
| 4,158,770 | A | 6/1979 | Davis |
| 4,210,811 | A | 7/1980 | Dennhoven |
| 4,216,499 | A | 8/1980 | Kunze et al. |
| 4,228,353 | A | 10/1980 | Johnson |
| 4,259,721 | A | 3/1981 | Kuznia |
| 4,266,425 | A | 5/1981 | Allport |
| 4,274,005 | A | 6/1981 | Yamamura |
| 4,297,580 | A | 10/1981 | Juner |
| 4,340,816 | A | 7/1982 | Schott |
| 4,352,021 | A | 9/1982 | Boyd |
| 4,366,382 | A | 12/1982 | Kotowski |
| 4,375,695 | A | 3/1983 | Harding |
| 4,384,209 | A | 5/1983 | Wagner |
| 4,399,403 | A | 8/1983 | Strandberg |
| 4,430,568 | A | 2/1984 | Yoshida |
| 4,468,802 | A | 8/1984 | Friedel |
| 4,471,343 | A | 9/1984 | Lemelson |
| 4,566,113 | A | 1/1986 | Doenges |
| 4,571,491 | A | 2/1986 | Vinegar |
| 4,599,740 | A | 7/1986 | Cable |
| 4,622,688 | A | 11/1986 | Diemer |
| 4,641,330 | A | 2/1987 | Herwig |
| 4,672,649 | A | 6/1987 | Rutt |
| 4,675,890 | A | 6/1987 | Plessis |
| 4,736,401 | A | 4/1988 | Donges |
| 4,754,469 | A | 6/1988 | Harding |
| 4,788,704 | A | 11/1988 | Donges |
| 4,788,706 | A | 11/1988 | Jacobson |
| 4,789,930 | A | 12/1988 | Sones |
| 4,825,454 | A | 4/1989 | Annis |
| RE32,961 | E | 6/1989 | Wagner |
| 4,866,745 | A | 9/1989 | Akai |
| 4,868,856 | A | 9/1989 | Frith |
| 4,884,289 | A | 11/1989 | Glockmann |
| 4,887,604 | A | 12/1989 | Shefer |
| 4,956,856 | A | 9/1990 | Harding |
| 4,975,968 | A | 12/1990 | Yukl |
| 4,979,202 | A | 12/1990 | Siczek |
| 4,987,584 | A | 1/1991 | Doenges |
| 4,991,189 | A | 2/1991 | Boomgaarden |
| 5,007,072 | A | 4/1991 | Jenkins |
| 5,008,911 | A | 4/1991 | Harding |
| 5,022,062 | A | 6/1991 | Annis |
| 5,033,106 | A | 7/1991 | Kita |
| 5,056,124 | A | 10/1991 | Kakimoto |
| 5,065,418 | A | 11/1991 | Bermbach |
| 5,081,456 | A | 1/1992 | Michiguchi |
| 5,091,924 | A | 2/1992 | Bermbach |
| 5,098,640 | A | 3/1992 | Gozani |
| 5,105,452 | A | 4/1992 | McInerney |
| 5,144,191 | A | 9/1992 | Jones et al. |
| 5,155,365 | A | 10/1992 | Cann |
| 5,172,401 | A | 12/1992 | Asari |
| 5,179,581 | A | 1/1993 | Annis |
| 5,181,234 | A | 1/1993 | Smith |
| 5,182,764 | A | 1/1993 | Peschmann |
| 5,224,144 | A | 6/1993 | Annis |
| 5,227,800 | A | 7/1993 | Huguenin |
| 5,237,598 | A | 8/1993 | Albert |
| 5,247,556 | A | 9/1993 | Eckert |
| 5,247,561 | A | 9/1993 | Kotowski |
| 5,253,283 | A | 10/1993 | Annis |
| 5,259,014 | A | 11/1993 | Brettschneider |
| 5,263,075 | A | 11/1993 | McGann |
| 5,265,144 | A | 11/1993 | Harding |
| 5,272,627 | A | 12/1993 | Maschhoff |
| 5,313,511 | A | 5/1994 | Annis |
| 5,319,547 | A | 6/1994 | Krug |
| 5,339,080 | A | 8/1994 | Steinway |
| 5,345,240 | A | 9/1994 | Frazier |
| 5,365,567 | A | 11/1994 | Ohtsuchi |
| 5,367,552 | A | 11/1994 | Peschmann |
| 5,379,334 | A | 1/1995 | Zimmer |
| 5,410,156 | A | 4/1995 | Miller |
| 5,412,702 | A | 5/1995 | Sata |
| 5,420,905 | A | 5/1995 | Bertozzi |
| 5,467,377 | A | 11/1995 | Dawson |
| 5,481,584 | A | 1/1996 | Tang |
| 5,490,196 | A | 2/1996 | Rudich |
| 5,490,218 | A | 2/1996 | Krug |
| 5,493,596 | A | 2/1996 | Annis |
| 5,511,104 | A | 4/1996 | Mueller |
| 5,524,133 | A | 6/1996 | Neale |
| 5,552,705 | A | 9/1996 | Keller |
| 5,557,108 | A | 9/1996 | Tumer |
| 5,557,283 | A | 9/1996 | Sheen |
| 5,570,403 | A | 10/1996 | Yamazaki |
| 5,600,303 | A | 2/1997 | Husseiny |
| 5,600,700 | A | 2/1997 | Krug |
| 5,604,778 | A | 2/1997 | Polacin |
| 5,606,167 | A | 2/1997 | Miller |
| 5,633,907 | A | 5/1997 | Gravelle |
| 5,638,420 | A | 6/1997 | Armistead |
| 5,642,393 | A | 6/1997 | Krug |
| 5,642,394 | A | 6/1997 | Rothschild |
| 5,648,997 | A | 7/1997 | Chao |
| 5,651,047 | A | 7/1997 | Moorman |
| 5,661,774 | A | 8/1997 | Gordon |
| 5,666,393 | A | 9/1997 | Annis |
| 5,687,210 | A | 11/1997 | Maitrejean |
| 5,689,239 | A | 11/1997 | Turner |
| 5,689,541 | A | 11/1997 | Schardt |
| 5,692,028 | A | 11/1997 | Geus |
| 5,712,926 | A | 1/1998 | Eberhard |
| 5,745,543 | A | 4/1998 | De |
| 5,751,837 | A | 5/1998 | Watanabe |
| 5,764,683 | A | 6/1998 | Swift |
| 5,768,334 | A | 6/1998 | Maitrejean |
| 5,787,145 | A | 7/1998 | Geus |
| 5,796,802 | A | 8/1998 | Gordon |
| 5,805,660 | A | 9/1998 | Perion |
| 5,812,630 | A | 9/1998 | Blaffert |
| 5,818,897 | A | 10/1998 | Gordon |

(56) References Cited

U.S. PATENT DOCUMENTS

| | | |
|---|---|---|
| 5,838,758 A | 11/1998 | Krug |
| 5,838,759 A | 11/1998 | Armistead |
| 5,841,831 A | 11/1998 | Hell |
| 5,859,891 A | 1/1999 | Hibbard |
| 5,881,122 A | 3/1999 | Crawford |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,910,973 A | 6/1999 | Grodzins |
| 5,930,326 A | 7/1999 | Rothschild |
| 5,940,468 A | 8/1999 | Huang |
| 5,943,388 A | 8/1999 | Tuemer |
| 5,966,422 A | 10/1999 | Dafni |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,135 A | 2/2000 | McFee |
| 6,026,143 A | 2/2000 | Simanovsky |
| 6,026,171 A | 2/2000 | Hiraoglu |
| 6,031,890 A | 2/2000 | Bermbach |
| 6,035,014 A | 3/2000 | Hiraoglu |
| 6,037,597 A | 3/2000 | Karavolos |
| 6,054,712 A | 4/2000 | Komardin |
| 6,058,158 A | 5/2000 | Eiler |
| 6,067,344 A | 5/2000 | Grodzins |
| 6,067,366 A | 5/2000 | Simanovsky |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,850 A | 9/2000 | Mayo |
| 6,118,852 A | 9/2000 | Rogers |
| 6,122,343 A | 9/2000 | Pidcock |
| 6,125,167 A | 9/2000 | Morgan |
| 6,128,365 A | 10/2000 | Bechwati |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,184,841 B1 | 2/2001 | Shober |
| 6,185,272 B1 | 2/2001 | Hiraoglu |
| 6,188,743 B1 | 2/2001 | Tybinkowski |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,216,540 B1 | 4/2001 | Nelson |
| 6,218,943 B1 | 4/2001 | Ellenbogen |
| 6,236,709 B1 | 5/2001 | Perry |
| 6,249,567 B1 | 6/2001 | Rothschild |
| 6,252,929 B1 | 6/2001 | Swift |
| 6,252,932 B1 | 6/2001 | Arakawa |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,288,676 B1 | 9/2001 | Maloney |
| 6,292,533 B1 | 9/2001 | Swift |
| 6,301,326 B2 | 10/2001 | Bjorkholm |
| 6,304,629 B1 | 10/2001 | Conway |
| 6,317,509 B1 | 11/2001 | Simanovsky |
| 6,320,933 B1 | 11/2001 | Grodzins |
| 6,324,249 B1 | 11/2001 | Fazzio |
| 6,342,696 B1 | 1/2002 | Chadwick |
| 6,345,113 B1 | 2/2002 | Crawford |
| 6,347,132 B1 | 2/2002 | Annis |
| 6,356,620 B1 | 3/2002 | Rothschild |
| 6,359,582 B1 | 3/2002 | MacAleese |
| 6,417,797 B1 | 7/2002 | Cousins |
| 6,418,189 B1 | 7/2002 | Schafer |
| 6,424,695 B1 | 7/2002 | Grodzins |
| 6,429,578 B1 | 8/2002 | Danielsson |
| 6,430,255 B2 | 8/2002 | Fenkart |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,453,003 B1 | 9/2002 | Springer |
| 6,453,007 B2 | 9/2002 | Adams |
| 6,456,093 B1 | 9/2002 | Merkel |
| 6,456,684 B1 | 9/2002 | Mun |
| 6,459,755 B1 | 10/2002 | Li |
| 6,459,761 B1 | 10/2002 | Grodzins et al. |
| 6,459,764 B1 | 10/2002 | Chalmers et al. |
| 6,469,624 B1 | 10/2002 | Whan |
| 6,473,487 B1 | 10/2002 | Le |
| RE37,899 E | 11/2002 | Grodzins |
| 6,480,141 B1 | 11/2002 | Toth |
| 6,483,894 B2 | 11/2002 | Hartick |
| 6,501,414 B2 | 12/2002 | Arndt |
| 6,507,025 B1 | 1/2003 | Verbinski et al. |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,563,906 B2 | 5/2003 | Hussein |
| 6,580,778 B2 | 6/2003 | Meder |
| 6,584,170 B2 | 6/2003 | Aust |
| 6,590,956 B2 | 7/2003 | Fenkart et al. |
| 6,597,760 B2 | 7/2003 | Beneke |
| 6,606,516 B2 | 8/2003 | Levine |
| 6,618,466 B1 | 9/2003 | Ning |
| 6,628,745 B1 | 9/2003 | Annis |
| 6,636,581 B2 | 10/2003 | Sorenson |
| 6,647,091 B2 | 11/2003 | Fenkart et al. |
| 6,647,094 B2 | 11/2003 | Harding et al. |
| 6,647,095 B2 | 11/2003 | Hsieh |
| 6,650,276 B2 | 11/2003 | Lawless |
| 6,653,588 B1 | 11/2003 | Gillard-Hickman |
| 6,658,087 B2 | 12/2003 | Chalmers |
| 6,661,866 B1 | 12/2003 | Limkeman |
| 6,663,280 B2 | 12/2003 | Doenges |
| 6,665,373 B1 | 12/2003 | Kotowski |
| 6,665,433 B2 | 12/2003 | Roder |
| 6,687,333 B2 | 2/2004 | Carroll et al. |
| 6,690,766 B2 | 2/2004 | Kresse |
| 6,707,879 B2 | 3/2004 | McClelland et al. |
| 6,715,533 B2 | 4/2004 | Kresse |
| 6,721,387 B1 | 4/2004 | Naidu et al. |
| 6,735,271 B1 | 5/2004 | Rand et al. |
| 6,737,652 B2 | 5/2004 | Lanza et al. |
| 6,748,043 B1 | 6/2004 | Dobbs |
| 6,754,298 B2 | 6/2004 | Fessler |
| 6,760,407 B2 | 7/2004 | Price et al. |
| 6,763,635 B1 | 7/2004 | Lowman |
| 6,768,317 B2 | 7/2004 | Moeller |
| 6,770,884 B2 | 8/2004 | Bryman |
| 6,775,348 B2 | 8/2004 | Hoffman |
| 6,785,357 B2 | 8/2004 | Bernardi |
| 6,785,359 B2 | 8/2004 | Lemaitre |
| 6,788,761 B2 | 9/2004 | Bijjani et al. |
| 6,798,863 B2 | 9/2004 | Sato |
| 6,807,248 B2 | 10/2004 | Mihara |
| 6,812,426 B1 | 11/2004 | Kotowski |
| 6,813,374 B1 | 11/2004 | Karimi et al. |

(56) References Cited

U.S. PATENT DOCUMENTS

| | | | |
|---|---|---|---|
| 6,816,571 | B2 | 11/2004 | Bijjani et al. |
| 6,827,265 | B2 | 12/2004 | Knowles et al. |
| 6,830,185 | B2 | 12/2004 | Tsikos et al. |
| 6,831,590 | B1 | 12/2004 | Steinway |
| 6,837,422 | B1 | 1/2005 | Meder |
| 6,837,432 | B2 | 1/2005 | Tsikos |
| 6,839,403 | B1 | 1/2005 | Kotowski et al. |
| 6,843,599 | B2 | 1/2005 | Le |
| 6,856,271 | B1 | 2/2005 | Hausner |
| 6,856,667 | B2 | 2/2005 | Ellengogen |
| 6,859,514 | B2 | 2/2005 | Hoffman |
| 6,876,322 | B2 | 4/2005 | Keller |
| 6,891,381 | B2 | 5/2005 | Bailey |
| 6,894,636 | B2 | 5/2005 | Anderton |
| 6,901,135 | B2 | 5/2005 | Fox et al. |
| 6,906,329 | B2 | 6/2005 | Bryman |
| 6,907,101 | B2 | 6/2005 | Hoffman |
| 6,920,196 | B2 | 7/2005 | Ueno |
| 6,920,197 | B2 | 7/2005 | Kang |
| 6,922,455 | B2 | 7/2005 | Jurczyk et al. |
| 6,922,460 | B2 | 7/2005 | Skatter et al. |
| 6,922,461 | B2 | 7/2005 | Kang et al. |
| 6,928,141 | B2 | 8/2005 | Carver |
| 6,933,504 | B2 | 8/2005 | Hoffman et al. |
| 6,934,354 | B2 | 8/2005 | Hoffman |
| 6,940,071 | B2 | 9/2005 | Ramsden et al. |
| 6,944,264 | B2 | 9/2005 | Bijjani et al. |
| 6,947,517 | B2 | 9/2005 | Hoffman |
| 6,950,492 | B2 | 9/2005 | Besson |
| 6,950,493 | B2 | 9/2005 | Besson |
| 6,952,163 | B2 | 10/2005 | Huey et al. |
| 6,953,935 | B1 | 10/2005 | Hoffman |
| 6,957,913 | B2 | 10/2005 | Renkart et al. |
| 6,962,289 | B2 | 11/2005 | Vatan et al. |
| 6,968,030 | B2 | 11/2005 | Hoffman |
| 6,968,034 | B2 | 11/2005 | Ellengogen |
| 6,971,577 | B2 | 12/2005 | Tsikos et al. |
| 6,973,158 | B2 | 12/2005 | Besson |
| 6,975,698 | B2 | 12/2005 | Katcha et al. |
| 6,975,703 | B2 | 12/2005 | Wilson et al. |
| 6,978,936 | B2 | 12/2005 | Tsikos et al. |
| 6,980,627 | B2 | 12/2005 | Qiu et al. |
| 6,990,171 | B2 | 1/2006 | Toth et al. |
| 6,990,172 | B2 | 1/2006 | Toth |
| 6,991,371 | B2 | 1/2006 | Georgeson et al. |
| 6,993,115 | B2 | 1/2006 | McGuire et al. |
| 6,996,209 | B2 | 2/2006 | Marek |
| 7,010,083 | B2 | 3/2006 | Hoffman |
| 7,012,256 | B1 | 3/2006 | Roos |
| 7,012,989 | B2 | 3/2006 | Holland |
| 7,016,459 | B2 | 3/2006 | Ellenbogen et al. |
| 7,020,241 | B2 | 3/2006 | Beneke et al. |
| 7,020,242 | B2 | 3/2006 | Ellenbogen |
| 7,023,950 | B1 | 4/2006 | Annis |
| 7,023,956 | B2 | 4/2006 | Heaton et al. |
| 7,023,957 | B2 | 4/2006 | Bijjani et al. |
| 7,027,553 | B2 | 4/2006 | Dunham et al. |
| 7,027,554 | B2 | 4/2006 | Gaultier et al. |
| 7,031,430 | B2 | 4/2006 | Kaucic, Jr. et al. |
| 7,031,434 | B1 | 4/2006 | Saunders et al. |
| 7,034,313 | B2 | 4/2006 | Hoffman |
| 7,039,154 | B1 | 5/2006 | Ellenbogen et al. |
| 7,039,159 | B2 | 5/2006 | Muenchau |
| 7,045,787 | B1 | 5/2006 | Verbinski et al. |
| 7,046,756 | B2 | 5/2006 | Hoffman |
| 7,046,761 | B2 | 5/2006 | Ellenbogen et al. |
| 7,050,529 | B2 | 5/2006 | Hoffman |
| 7,050,536 | B1 | 5/2006 | Fenkart et al. |
| 7,050,540 | B2 | 5/2006 | Wilkins |
| 7,054,408 | B2 | 5/2006 | Jiang et al. |
| 7,062,009 | B2 | 6/2006 | Karimi et al. |
| 7,062,011 | B1 | 6/2006 | Tybinkowski et al. |
| 7,062,074 | B1 | 6/2006 | Beneke |
| 7,064,334 | B2 | 6/2006 | Hoffman et al. |
| 7,065,175 | B2 | 6/2006 | Green |
| 7,065,179 | B2 | 6/2006 | Block et al. |
| 7,068,749 | B2 | 6/2006 | Kollegal et al. |
| 7,068,750 | B2 | 6/2006 | Toth et al. |
| 7,068,751 | B2 | 6/2006 | Toth |
| 7,072,434 | B1 | 7/2006 | Tybinkowski et al. |
| 7,076,029 | B2 | 7/2006 | Toth et al. |
| 7,078,699 | B2 | 7/2006 | Seppi |
| 7,081,628 | B2 | 7/2006 | Granfors et al. |
| 7,084,404 | B2 | 8/2006 | Hoffman et al. |
| 7,087,902 | B2 | 8/2006 | Wang et al. |
| 7,088,799 | B2 | 8/2006 | Hoffman |
| 7,090,133 | B2 | 8/2006 | Zhu |
| 7,092,481 | B2 | 8/2006 | Hoffman |
| 7,092,485 | B2 | 8/2006 | Kravis |
| 7,103,137 | B2 | 9/2006 | Seppi et al. |
| 7,110,488 | B2 | 9/2006 | Katcha et al. |
| 7,112,797 | B2 | 9/2006 | Hoge |
| 7,116,749 | B2 | 10/2006 | Besson |
| 7,116,751 | B2 | 10/2006 | Ellenbogen et al. |
| 7,119,553 | B2 | 10/2006 | Yang et al. |
| 7,120,222 | B2 | 10/2006 | Hoffman |
| 7,123,681 | B2 | 10/2006 | Ellenbogen et al. |
| 7,127,027 | B2 | 10/2006 | Hoffman |
| 7,130,374 | B1 | 10/2006 | Jacobs et al. |
| 7,133,491 | B2 | 11/2006 | Bernardi et al. |
| 7,136,450 | B2 | 11/2006 | Ying et al. |
| 7,136,451 | B2 | 11/2006 | Naidu et al. |
| 7,139,367 | B1 | 11/2006 | Le |
| 7,139,406 | B2 | 11/2006 | McClelland et al. |
| 7,142,629 | B2 | 11/2006 | Edie et al. |
| 7,149,278 | B2 | 12/2006 | Arenson et al. |
| 7,149,339 | B2 | 12/2006 | Veneruso |
| 7,155,812 | B1 | 1/2007 | Peterson et al. |
| 7,158,611 | B2 | 1/2007 | Heismann et al. |
| 7,164,747 | B2 | 1/2007 | Ellenbogen et al. |
| 7,164,750 | B2 | 1/2007 | Nabors et al. |
| 7,166,458 | B2 | 1/2007 | Ballerstadt et al. |
| 7,167,539 | B1 | 1/2007 | Hoffman |
| 7,173,998 | B2 | 2/2007 | Hoffman et al. |
| 7,177,387 | B2 | 2/2007 | Yasunaga et al. |
| 7,177,391 | B2 | 2/2007 | Chapin et al. |
| 7,183,906 | B2 | 2/2007 | Zanovitch |
| 7,187,756 | B2 | 3/2007 | Gohno |
| 7,190,757 | B2 | 3/2007 | Ying et al. |
| 7,192,031 | B2 | 3/2007 | Dunham et al. |
| 7,197,113 | B1 | 3/2007 | Katcha et al. |
| 7,197,116 | B2 | 3/2007 | Dunham |
| 7,197,172 | B1 | 3/2007 | Naidu et al. |
| 7,203,269 | B2 | 4/2007 | Huber |
| 7,203,271 | B2 | 4/2007 | Benz |
| 7,203,629 | B2 | 4/2007 | Ozis et al. |
| 7,206,379 | B2 | 4/2007 | Lemaitre |
| 7,207,713 | B2 | 4/2007 | Lowman |
| 7,215,731 | B1 | 5/2007 | Basu et al. |
| 7,215,738 | B2 | 5/2007 | Muenchau et al. |
| 7,218,700 | B2 | 5/2007 | Huber et al. |
| 7,218,704 | B1 | 5/2007 | Adams et al. |
| 7,224,763 | B2 | 5/2007 | Naidu et al. |
| 7,224,765 | B2 | 5/2007 | Ellenbogen |
| 7,224,766 | B2 | 5/2007 | Jiang et al. |
| 7,224,769 | B2 | 5/2007 | Turner |
| 7,233,640 | B2 | 6/2007 | Ikhlef et al. |
| 7,233,644 | B1 | 6/2007 | Bendahan |
| 7,236,564 | B2 | 6/2007 | Hopkins et al. |
| 7,238,945 | B2 | 7/2007 | Hoffman et al. |
| 7,247,856 | B2 | 7/2007 | Hoge |
| 7,251,310 | B2 | 7/2007 | Smith |
| 7,260,170 | B2 | 8/2007 | Arenson et al. |
| 7,260,171 | B1 | 8/2007 | Arenson |
| 7,260,172 | B2 | 8/2007 | Arenson |
| 7,260,173 | B2 | 8/2007 | Wakayama et al. |
| 7,260,174 | B2 | 8/2007 | Hoffman et al. |
| 7,260,182 | B2 | 8/2007 | Toth et al. |
| 7,263,160 | B2 | 8/2007 | Schlomka et al. |
| 7,266,180 | B1 | 9/2007 | Saunders et al. |
| 7,272,429 | B2 | 9/2007 | Walker et al. |
| 7,274,767 | B2 | 9/2007 | Clayton et al. |
| 7,277,577 | B2 | 10/2007 | Ying et al. |
| 7,279,120 | B2 | 10/2007 | Cheng et al. |

(56) References Cited

U.S. PATENT DOCUMENTS

| | | |
|---|---|---|
| 7,280,631 B2 | 10/2007 | De Man et al. |
| 7,282,727 B2 | 10/2007 | Retsky |
| 7,283,604 B2 | 10/2007 | De Man et al. |
| 7,283,609 B2 | 10/2007 | Possin et al. |
| 7,295,019 B2 | 11/2007 | Yang et al. |
| 7,295,651 B2 | 11/2007 | Delgado et al. |
| 7,298,812 B2 | 11/2007 | Tkaczyk et al. |
| 7,302,083 B2 | 11/2007 | Larson et al. |
| 7,308,073 B2 | 12/2007 | Tkaczyk et al. |
| 7,308,074 B2 | 12/2007 | Jiang et al. |
| 7,308,077 B2 | 12/2007 | Bijjani et al. |
| 7,317,195 B2 | 1/2008 | Eikman |
| 7,317,390 B2 | 1/2008 | Huey et al. |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying et al. |
| 7,330,527 B2 | 2/2008 | Hoffman et al. |
| 7,330,535 B2 | 2/2008 | Arenson et al. |
| 7,333,587 B2 | 2/2008 | De |
| 7,333,588 B2 | 2/2008 | Mistretta et al. |
| 7,333,589 B2 | 2/2008 | Ellenbogen et al. |
| 7,335,887 B1 | 2/2008 | Verbinski et al. |
| 7,336,769 B2 | 2/2008 | Arenson et al. |
| 7,340,525 B1 | 3/2008 | Bhatia et al. |
| 7,349,525 B2 | 3/2008 | Morton et al. |
| 7,369,640 B2 | 5/2008 | Seppi |
| 7,369,643 B2 | 5/2008 | Kotowski |
| 7,372,934 B2 | 5/2008 | De |
| 7,400,701 B1 | 7/2008 | Cason |
| 7,440,543 B2 | 10/2008 | Morton |
| 7,486,760 B2 | 2/2009 | Harding |
| 7,486,769 B2 | 2/2009 | Brondo |
| 7,492,855 B2 | 2/2009 | Hopkins et al. |
| 7,505,563 B2 | 3/2009 | Morton |
| 7,512,215 B2 | 3/2009 | Morton et al. |
| 7,564,939 B2 | 7/2009 | Morton |
| 7,579,845 B2 | 8/2009 | Peschmann |
| 7,590,215 B2 | 9/2009 | Schlomka |
| 7,593,506 B2 | 9/2009 | Cason |
| 7,596,275 B1 | 9/2009 | Richardson |
| 7,636,638 B2 | 12/2009 | Russ |
| 7,643,866 B2 | 1/2010 | Heismann |
| 7,649,981 B2 | 1/2010 | Seppi |
| 7,664,230 B2 | 2/2010 | Morton |
| 7,684,538 B2 | 3/2010 | Morton |
| 7,724,868 B2 | 5/2010 | Morton |
| 7,734,066 B2 | 6/2010 | Delia |
| 7,769,132 B1 | 8/2010 | Hurd |
| 7,778,382 B2 | 8/2010 | Hoffman |
| 7,835,495 B2 | 11/2010 | Harding |
| 7,876,879 B2 | 1/2011 | Morton |
| 7,903,789 B2 | 3/2011 | Morton |
| 7,929,663 B2 | 4/2011 | Morton |
| 7,949,101 B2 | 5/2011 | Morton |
| 8,135,110 B2 | 3/2012 | Morton |
| 8,138,770 B2 | 3/2012 | Peschmann |
| 8,243,876 B2 | 8/2012 | Morton |
| 8,837,669 B2 * | 9/2014 | Morton .............. A61B 6/022 378/41 |
| 2001/0022346 A1 | 9/2001 | Katagami et al. |
| 2001/0033635 A1 | 10/2001 | Kuwabara |
| 2001/0050972 A1 | 12/2001 | Yamada |
| 2002/0008655 A1 | 1/2002 | Haj-Yousef |
| 2002/0031202 A1 | 3/2002 | Callerame |
| 2002/0094064 A1 | 7/2002 | Zhou |
| 2002/0094117 A1 | 7/2002 | Funahashi |
| 2002/0097836 A1 | 7/2002 | Grodzins |
| 2002/0101958 A1 | 8/2002 | Bertsche |
| 2002/0176531 A1 | 11/2002 | McClelland |
| 2003/0009202 A1 | 1/2003 | Levine |
| 2003/0021377 A1 | 1/2003 | Turner et al. |
| 2003/0031352 A1 | 2/2003 | Nelson et al. |
| 2003/0048868 A1 | 3/2003 | Bailey |
| 2003/0053597 A1 | 3/2003 | Flohr |
| 2003/0076921 A1 | 4/2003 | Mihara |
| 2003/0076924 A1 | 4/2003 | Mario |
| 2003/0085163 A1 | 5/2003 | Chan |
| 2003/0108155 A1 | 6/2003 | Wilkins |
| 2003/0179126 A1 | 9/2003 | Jablonski |
| 2003/0190011 A1 | 10/2003 | Beneke |
| 2003/0216644 A1 | 11/2003 | Hall |
| 2004/0010127 A1 | 1/2004 | Linder |
| 2004/0017224 A1 | 1/2004 | Tumer |
| 2004/0017888 A1 | 1/2004 | Seppi et al. |
| 2004/0077943 A1 | 4/2004 | Meaney |
| 2004/0081270 A1 | 4/2004 | Heuscher |
| 2004/0096030 A1 | 5/2004 | Banchieri |
| 2004/0101098 A1 | 5/2004 | Bijjani |
| 2004/0120454 A1 | 6/2004 | Ellenbogen et al. |
| 2004/0141584 A1 | 7/2004 | Bernardi |
| 2004/0213378 A1 | 10/2004 | Zhou et al. |
| 2004/0213379 A1 | 10/2004 | Bittl |
| 2004/0223585 A1 | 11/2004 | Heismann |
| 2004/0232054 A1 | 11/2004 | Brown |
| 2004/0245449 A1 | 12/2004 | Nakashige |
| 2004/0252807 A1 | 12/2004 | Skatter |
| 2004/0258198 A1 | 12/2004 | Carver |
| 2004/0258305 A1 | 12/2004 | Burnham |
| 2005/0008073 A1 | 1/2005 | Techmer |
| 2005/0031075 A1 | 2/2005 | Hopkins |
| 2005/0053189 A1 | 3/2005 | Gohno |
| 2005/0058242 A1 | 3/2005 | Peschmann |
| 2005/0084069 A1 | 4/2005 | Du |
| 2005/0084073 A1 | 4/2005 | Seppi |
| 2005/0089140 A1 | 4/2005 | Mario |
| 2005/0105682 A1 | 5/2005 | Heumann |
| 2005/0111610 A1 | 5/2005 | Heumann |
| 2005/0111619 A1 | 5/2005 | Bijjani |
| 2005/0157925 A1 | 7/2005 | Lorenz |
| 2005/0169422 A1 | 8/2005 | Ellenbogen |
| 2005/0169423 A1 | 8/2005 | Ellenbogen |
| 2005/0180542 A1 | 8/2005 | Leue |
| 2005/0190882 A1 | 9/2005 | McGuire |
| 2005/0226364 A1 | 10/2005 | Bernard De Man et al. |
| 2005/0238232 A1 | 10/2005 | Ying |
| 2005/0249416 A1 | 11/2005 | Leue |
| 2005/0281390 A1 | 12/2005 | Johnson et al. |
| 2006/0002585 A1 | 1/2006 | Larson |
| 2006/0008047 A1 | 1/2006 | Zhou |
| 2006/0018428 A1 | 1/2006 | Li et al. |
| 2006/0109949 A1 | 5/2006 | Tkaczyk |
| 2006/0113163 A1 | 6/2006 | Hu et al. |
| 2006/0133571 A1 | 6/2006 | Winsor |
| 2006/0145771 A1 | 7/2006 | Strange |
| 2006/0233295 A1 | 10/2006 | Edic |
| 2006/0273259 A1 | 12/2006 | Li et al. |
| 2006/0280286 A1 | 12/2006 | Kaval |
| 2007/0003003 A1 | 1/2007 | Seppi et al. |
| 2007/0025512 A1 | 2/2007 | Gertsenshteyn |
| 2007/0053495 A1 | 3/2007 | Morton et al. |
| 2007/0096030 A1 | 5/2007 | Li et al. |
| 2007/0110215 A1 | 5/2007 | Li |
| 2007/0122003 A1 | 5/2007 | Dobkin |
| 2007/0133740 A1 | 6/2007 | Kang et al. |
| 2007/0172024 A1 | 7/2007 | Morton et al. |
| 2007/0183568 A1 | 8/2007 | Kang et al. |
| 2007/0189597 A1 | 8/2007 | Limer |
| 2007/0237288 A1 | 10/2007 | Tkaczyk |
| 2007/0242802 A1 | 10/2007 | Dafni |
| 2007/0263767 A1 | 11/2007 | Brondo |
| 2008/0043912 A1 | 2/2008 | Harding |
| 2008/0056432 A1 | 3/2008 | Pack |
| 2008/0056435 A1 | 3/2008 | Basu et al. |
| 2008/0198967 A1 | 8/2008 | Connelly |
| 2008/0237480 A1 | 10/2008 | Robinson |
| 2008/0267355 A1 | 10/2008 | Morton |
| 2009/0003514 A1 | 1/2009 | Edic |
| 2009/0010386 A1 | 1/2009 | Peschmann |
| 2009/0034792 A1 | 2/2009 | Kennison |
| 2009/0161816 A1 | 6/2009 | De |
| 2009/0207967 A1 | 8/2009 | Liu |
| 2009/0265386 A1 | 10/2009 | March |

(56) References Cited

U.S. PATENT DOCUMENTS

| | | | |
|---|---|---|---|
| 2010/0020920 A1 | 1/2010 | Mertelmeier | |
| 2010/0020934 A1 | 1/2010 | Morton | |
| 2010/0329532 A1 | 12/2010 | Masuda | |

FOREIGN PATENT DOCUMENTS

| | | |
|---|---|---|
| CA | 2365045 | 6/2003 |
| CN | 85107860 A | 10/1986 |
| CN | 1050769 | 4/1991 |
| CN | 1130498 A | 9/1996 |
| CN | 1309768 | 8/2001 |
| CN | 1550215 A | 12/2004 |
| CN | 1626039 A | 6/2005 |
| CN | 1708256 A | 12/2005 |
| CN | 1795527 A | 6/2006 |
| CN | 100371689 C | 7/2006 |
| DE | 2729353 A1 | 1/1979 |
| DE | 4410757 A1 | 1/1995 |
| DE | 4436688 A1 | 4/1996 |
| DE | 102004056590 A1 | 6/2005 |
| EP | 0198276 A1 | 10/1986 |
| EP | 0424912 A2 | 5/1991 |
| EP | 0432568 | 6/1991 |
| EP | 0531993 A1 | 3/1993 |
| EP | 0584871 A1 | 3/1994 |
| EP | 0795919 A2 | 9/1997 |
| EP | 0873511 A1 | 10/1998 |
| EP | 0924742 A2 | 6/1999 |
| EP | 0930046 A2 | 7/1999 |
| EP | 1277439 A1 | 1/2003 |
| EP | 1298055 A2 | 4/2003 |
| EP | 1371970 A2 | 12/2003 |
| EP | 1374776 A1 | 1/2004 |
| EP | 1540318 A1 | 6/2005 |
| EP | 1558142 A1 | 8/2005 |
| EP | 1618584 A2 | 1/2006 |
| EP | 1689640 A2 | 8/2006 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2133208 | 7/1984 |
| GB | 2212903 A | 8/1989 |
| GB | 2329817 A | 3/1995 |
| GB | 2285506 A | 7/1995 |
| GB | 2299251 | 9/1996 |
| GB | 2356453 A | 5/2001 |
| GB | 2414072 A | 11/2005 |
| GB | 2416655 A | 2/2006 |
| GB | 2416944 A | 2/2006 |
| GB | 2417821 A | 3/2006 |
| GB | 2418529 A | 3/2006 |
| GB | 2423687 A | 8/2006 |
| GB | 2437777 A | 11/2007 |
| GB | 2471421 A | 12/2010 |
| JP | 50012990 | 2/1975 |
| JP | S5427793 | 3/1979 |
| JP | 570175247 | 10/1982 |
| JP | 590016254 A | 1/1984 |
| JP | S5916254 A | 1/1984 |
| JP | 59075549 | 4/1984 |
| JP | 59174744 | 10/1984 |
| JP | 600015546 | 1/1985 |
| JP | S601554 A | 1/1985 |
| JP | S602144 | 1/1985 |
| JP | 600021440 | 2/1985 |
| JP | 60073442 A | 4/1985 |
| JP | S61028039 | 2/1986 |
| JP | 62064977 | 3/1987 |
| JP | 64034333 A | 2/1989 |
| JP | 05100037 A | 4/1993 |
| JP | 05192327 A | 8/1993 |
| JP | H05060381 | 9/1993 |
| JP | 5325851 | 12/1993 |
| JP | 060038957 | 2/1994 |
| JP | H06169911 | 6/1994 |
| JP | 6296607 | 10/1994 |
| JP | H07012756 | 1/1995 |
| JP | H07057113 | 3/1995 |
| JP | H08178872 | 7/1996 |
| JP | H08299322 | 11/1996 |
| JP | 10005206 A | 1/1998 |
| JP | H10001209 | 1/1998 |
| JP | 10075944 A | 3/1998 |
| JP | 1998075944 A | 3/1998 |
| JP | 10506195 | 6/1998 |
| JP | H10211196 A | 8/1998 |
| JP | 11146871 A | 6/1999 |
| JP | 11262486 A | 9/1999 |
| JP | 2000107173 A | 4/2000 |
| JP | 2001083171 | 3/2001 |
| JP | 2001176408 A | 6/2001 |
| JP | 2001233440 | 8/2001 |
| JP | 2002039966 | 2/2002 |
| JP | 2002503816 | 2/2002 |
| JP | 2002162472 | 6/2002 |
| JP | 2002168805 | 6/2002 |
| JP | 2002195961 | 7/2002 |
| JP | 2002320610 A | 11/2002 |
| JP | 2002370814 | 12/2002 |
| JP | 2003126075 A | 5/2003 |
| JP | 2003135442 | 5/2003 |
| JP | 2004000605 A | 1/2004 |
| JP | 2004079128 A | 3/2004 |
| JP | 2004226253 | 8/2004 |
| JP | 2004233206 | 8/2004 |
| JP | 2005013768 A | 1/2005 |
| JP | 2005110722 | 4/2005 |
| JP | 2005177469 A | 7/2005 |
| JP | 2005534009 A | 11/2005 |
| JP | 2006502386 | 1/2006 |
| JP | 2006071514 | 3/2006 |
| JP | 2006167463 | 6/2006 |
| JP | 2006518039 | 8/2006 |
| JP | 2006320464 | 11/2006 |
| JP | 2006524809 A | 11/2006 |
| JP | 2007010455 | 1/2007 |
| JP | 2007500357 A | 1/2007 |
| JP | 2007508561 A | 4/2007 |
| JP | 2007533993 A | 11/2007 |
| JP | 2008178714 | 8/2008 |
| JP | 2008212840 | 9/2008 |
| JP | 2008268035 | 11/2008 |
| JP | 3147024 | 12/2008 |
| JP | 2009519457 | 5/2009 |
| NL | 1021026 | 1/2004 |
| NL | 1027596 C2 | 11/2005 |
| WO | 9217771 A1 | 10/1992 |
| WO | 9528715 A2 | 10/1995 |
| WO | 9718462 A1 | 5/1997 |
| WO | 9941676 | 8/1999 |
| WO | 9950882 | 10/1999 |
| WO | 9960387 A2 | 11/1999 |
| WO | 0231857 | 4/2002 |
| WO | 0231857 A1 | 4/2002 |
| WO | 03029844 | 4/2003 |
| WO | 03042674 | 5/2003 |
| WO | 03051201 | 6/2003 |
| WO | 03051201 A2 | 6/2003 |
| WO | 03065772 | 8/2003 |
| WO | 03105159 | 12/2003 |
| WO | 2004008968 A1 | 1/2004 |
| WO | 2004008970 A1 | 1/2004 |
| WO | 2004010127 A1 | 1/2004 |
| WO | 2004010381 A1 | 1/2004 |
| WO | 2004031755 | 4/2004 |
| WO | 2004031755 A2 | 4/2004 |
| WO | 2004037088 | 5/2004 |
| WO | 2004054329 A2 | 6/2004 |
| WO | 2004096050 | 11/2004 |
| WO | 2004097344 A2 | 11/2004 |
| WO | 2004097386 A1 | 11/2004 |
| WO | 2004097886 A2 | 11/2004 |

(56) References Cited

FOREIGN PATENT DOCUMENTS

| WO | 2004097888 | A2 | 11/2004 |
|---|---|---|---|
| WO | 2004097889 | A2 | 11/2004 |
| WO | 2004105610 | A | 12/2004 |
| WO | 2004111625 | | 12/2004 |
| WO | 2005017566 | A2 | 2/2005 |
| WO | 2005050405 | A2 | 6/2005 |
| WO | 2005084351 | | 9/2005 |
| WO | 2005095931 | | 10/2005 |
| WO | 2005102170 | | 11/2005 |
| WO | 2006027122 | A1 | 3/2006 |
| WO | 2006047718 | | 5/2006 |
| WO | 2006135586 | | 12/2006 |
| WO | 2006137919 | | 12/2006 |
| WO | 2007051418 | | 5/2007 |
| WO | 2007068933 | | 6/2007 |
| WO | 2007068933 | A1 | 6/2007 |
| WO | 2007076707 | | 7/2007 |
| WO | 2007079675 | | 7/2007 |
| WO | 2008018021 | | 2/2008 |
| WO | 2008027703 | A2 | 3/2008 |
| WO | 2008094305 | | 8/2008 |
| WO | 2009005932 | | 1/2009 |
| WO | 2009006044 | | 1/2009 |
| WO | 2009024817 | | 2/2009 |
| WO | 2009025935 | | 2/2009 |
| WO | 2010097621 | A2 | 9/2010 |
| WO | 2010138607 | A1 | 12/2010 |
| WO | 2012115629 | A1 | 8/2012 |

OTHER PUBLICATIONS

Great Britain Patent Application No. GB1017187.4, Combined Search and Examination Report, Jun. 21, 2007, CXR Limited.

Development of ultra-fast X-ray computed tomography scanner system, INS 98-43 6068772 A9823-8760J-016 (PHA); B9812-7510B-113 (EEA) NDN-174-0606-8771-7, Hori, K.; Fujimoto, T.; Kawanishi, K., Editor—Nalcioglu, O., Abbreviated Journal Title—1997 IEEE Nuclear Science Symposium, Conference Record (Cat. No. 97CH36135), Part No. vol. 2, 1997, pp. 1003-1008 vol. 2, 2 vol. xlviii+1761 pages(s), ISBN—0 7803 4258 5.

International Search Report, PCT/US2010/36221, Aug. 23, 2010, Rapiscan Security Productions, Inc.

International Search Report, PCT/US2011/25777, Jul. 26, 2011, Rapiscan Systems, Inc.

International Search Report, PCT/GB2006/004684, May 23, 2007, CXR Ltd.

International Search Report, PCT/GB2004/001729, Aug. 12, 2004, Rapiscan Systems, Inc.

International Search Report, PCT/GB2004/001731, May 27, 2005.

International Search Report, PCT/GB2004/001751, Mar. 21, 2005.

International Search Report, PCT/GB2004/001747, Aug. 10, 2004.

Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.

International Search Report, PCT/GB2004/001732, Feb. 25, 2005.

International Search Report, PCT/GB2004/001741, Mar. 3, 2005.

Office Action for Japanese Patent Application No. 2014-266203, Nov. 24, 2015.

Office Action for Japanese Patent Application No. 2014-266203, Jul. 25, 2016.

Office Action for Japanese Patent Application No. 2014-266204, Nov. 24, 2015.

Final Office Action for Japanese Patent Application No. 2014-266204, Jun. 30, 2016.

Office Action for Japanese Patent Application No. 2014-266205, Nov. 24, 2015.

* cited by examiner

X-RAY SCANNING SYSTEM

CROSS-REFERENCE TO RELATED APPLICATIONS

The present application is a continuation of U.S. patent application Ser. No. 13/304,738, filed on Nov. 28, 2011, which, in turn, is a continuation of U.S. patent application Ser. No. 12/697,073, filed on Jan. 29, 2010, and now U.S. Pat. No. 8,085,897, issued on Dec. 27, 2011, which, in turn, is a continuation of U.S. patent application Ser. No. 10/554,570, issued as U.S. Pat. No. 7,684,538, issued on Mar. 23, 2010, which is a National Stage Application of PCT/GB2004/001747, filed on Apr. 23, 2004 and which calls priority to Great Britain Patent Application Number 0309379.6, filed on Apr. 25, 2003, for priority.

All of the above-mentioned priority applications are herein incorporated by reference in their entirety.

FIELD OF THE INVENTION

The present invention relates to X-ray scanning It has particular application in medical computed tomography (CT) scanning, although it could equally be used in other suitable applications.

BACKGROUND OF THE INVENTION

X-ray computed tomography scanners have been used in medical imaging for many years. A conventional system comprises an X-ray tube that is rotated about an axis with an arcuate X-ray detector array also rotated at the same speed around the same axis. The patient is placed with their centre of gravity close to the axis of rotation, and moved along the axis as the tube is rotated. A fan-beam of X-radiation passes from the source through the patient to the X-ray detector array.

The X-ray detector array records the intensity of X-rays passed through the patient at each location along its length. From these recorded X-ray intensities, it is possible to form a tomographic (cross-sectional) image, typically by means of a filtered back projection algorithm, if one set of projection data is recorded at each source angle. In order to produce an accurate tomographic image of an object, such as a part of the patient, it can be shown to be a requirement that the X-ray source pass through every plane through the object. In the arrangement described above, this is achieved by the rotational scanning of the X-ray source and the longitudinal movement of the patient.

In this type of system the rate at which X-ray tomographic scans can be collected is dependent on the speed of rotation of the gantry that holds the X-ray source and detector array. In a modern medical gantry, the entire tube-detector assembly and gantry will complete two revolutions per second. This allows up to four tomographic scans to be collected per second.

As the state-of-the-art has developed, the single ring of X-ray detectors has been replaced by multiple rings of X-ray detectors. This allows many slices (typically up to 8) to be scanned simultaneously and reconstructed using filtered back projection methods adapted from the single scan machines. In a further improvement of this process, the patient position may be moved along the axis of the scanner such that the source describes a helical motion about the patient. This allows a more sophisticated cone beam image reconstruction method to be applied that can in principle offer a more accurate volume image reconstruction. The combination of physical motion of the patient and source rotation about the patient when combined with multiple ring X-ray detectors allows volume images of the patient to be obtained over a period of several seconds.

SUMMARY OF THE INVENTION

Swept electron beam scanners have been demonstrated whereby the mechanical scanning motion of the X-ray source and X-ray detectors is eliminated, being replaced by a continuous ring (or rings) of X-ray detectors that surrounds the patient with a moving X-ray source being generated as a result of sweeping an electron beam around an arcuate anode. This allows images to be obtained more rapidly than in conventional scanners. By simultaneous movement of the patient along the axis of the scanner, volume image data may be acquired in timescales of the order of a second.

The present invention provides an X-ray imaging system comprising a multi-focus X-ray source extending around an imaging volume to be imaged by the system, and defining a locus of source points from which X-rays can be directed through the imaging volume, and an X-ray detector array also extending around the imaging volume and arranged to detect X-rays from the source points which have passed through the imaging volume, wherein the source points are arranged to follow a three-dimensional locus around the imaging volume such that data from the detector array can be used to produce a three dimensional tomographic image of a stationary object within the imaging volume.

Preferably the detector array is substantially cylindrical and said locus covers at least half of the circumference of the cylinder, more preferably the full circumference, and substantially the whole of the length of the cylinder. More preferably the locus is substantially helical.

However, it will be appreciated that other locus configurations could equally be used which would enable the object in the imaging volume to be fully tomographically imaged. Preferably the locus passes through substantially every plane which passes through the imaging volume.

The system preferably further comprises control means arranged to scan the imaging volume by activating each of the X-ray source points and collecting respective image data sets, and imaging means arranged to produce a three-dimensional image of the imaging volume from the data sets. Preferably the control means is arranged to scan the imaging volume repeatedly to produce consecutive images of the imaged volume. Still more preferably the system further comprises display means arranged to display the consecutive images to produce a real-time video image of the imaged volume.

Preferably the control means is further arranged to activate one of the source points to produce a plane image of an object and to store the plane image for display. More preferably the control means is arranged to activate said one of the source points repeatedly thereby to produce a series of plane images, and to display the plane images in sequence to produce a plane video image. Still more preferably the control means is arranged to alternate between a first mode in which it produces a plane image data set and a second mode in which it produces a tomographic image data set, and to process the data sets to produce a combined image data set for producing a combined display.

The plane image may comprise a fluoroscopic image. Such plane images, especially when used to generate a real time video image, are used for a variety of purposes, including the monitoring of medical operations where the position of instruments such as catheters inside a patient can be monitored in real time.

Indeed, the present invention further provides an X-ray imaging system comprising an X-ray source defining plurality of source points around an imaging volume from which X-rays can be directed through the imaging volume, and an X-ray detector array extending around the imaging volume and arranged to detect X-rays from the source points which have passed through the imaging volume, and control means arranged to alternate between a first mode in which it controls the source to produce X-rays from one of the source points to produce a plane image data set and a second mode in which it controls the source to produce X-rays from each of the source points to produce a tomographic image data set, and to process the data sets to produce a combined image data set for producing a combined display.

Rather than producing just one plane image, a plurality of source points can be used to produce a plurality of plane images in different planes. The control means may arranged to activate a further one of source points close to said one of the source points whereby a pair of data sets are produced, and to combine the data sets so that the plane image or each of the plane images is a stereo image. Preferably the control means is arranged to process the data sets by mapping features from one of the data sets onto the other of the data sets thereby to enhance the image produced from said other of the data sets.

BRIEF DESCRIPTION OF THE DRAWINGS

Preferred embodiments of the present invention will now be described by way of example only with reference to the accompanying drawings in which.

DETAILED DESCRIPTION OF THE INVENTION

Figure 1:
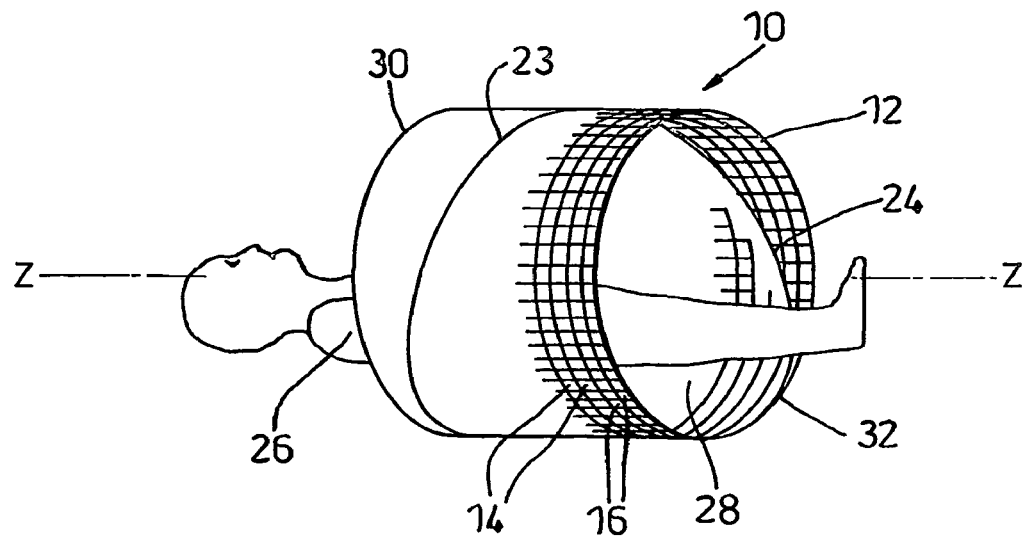
FIG. 1 is a schematic perspective view of an X-ray scanner according to a first embodiment of the invention.

Referring to FIG. 1, an X-ray scanner 10 comprises a cylindrical multi-element detector array 12 formed from many hundred individual rings 14 of detector elements 16. Each ring 14 may typically be of width 1-3 mm with centre-to-centre spacing between individual detector elements in the ring of 1-3 mm. The diameter of the detector array 12 is typically in the range 60-80 cm. The individual detector elements 16 should preferably have good efficiency at detecting X-rays and can be manufactured, for example, from high density scintillators, semiconductor materials or pressurized gas ionization chambers. The detector array 12 has a longitudinal central axis Z, and is arranged to enable a patient 18 to be placed inside the array 12 approximately on the central axis Z.

Figure 2:
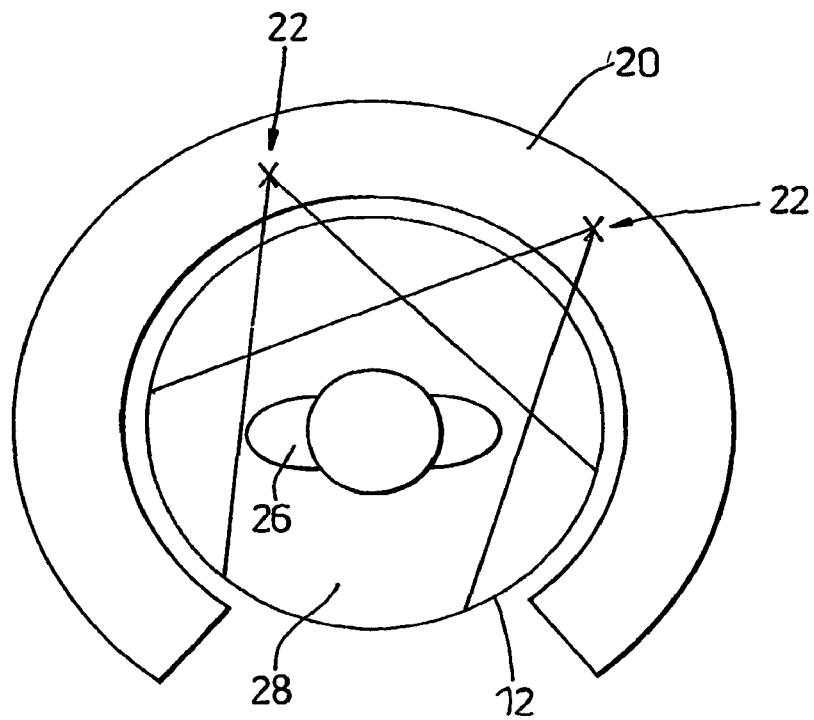
FIG. 2 is a cross section through the scanner of FIG. 1.

A multi focus X-ray source 20 is wrapped around the outside of the X-ray sensor array 12 in a helical manner as shown in FIG. 2. The source 20 allows X-rays to be emitted from each of a number of source points 22 spaced along the source 20. X-rays from the multi focus X-ray source 20 pass through a clear helical slot 24 that is present in the detector array 12 and aligned with the source points 22 such that, for each source point 22, the X-rays irradiate a group of the X-ray detector elements 16 on the opposite side of the detector array 12.

The slot 24 in the detector array 12 is cut in a way that leads to the locus 23 of source points 22 as shown in FIG. 1. This helical slot 24, and the resulting helical source trajectory, means that the set of data collected following X-ray transmission through the patient 26 is mathematically sufficient to form a true three dimensional image reconstruction. This is because the locus 23 of source points 22 passes through every plane passing through the scanning volume 28 which is essentially defined as the volume within the sensor array 12, i.e. radially inside the array 12 and between its two longitudinal ends 30, 32.

The multi-focus X-ray source 20 comprises a continuous anode held at a high positive potential with respect to a plurality of grid controlled electron emitters. Each emitter is "turned on" in turn and the corresponding electron beam irradiates the target, so producing X-radiation from a respective source point 22. By changing the active grid controlled electron emitter, the effect of moving the X-ray source around the patient can be obtained. The X-ray source 20 is housed in a thick housing to avoid irradiating X-ray detectors 16 and other components in the system close to the X-ray source 20. An example of a suitable source is described in our co-pending UK patent application No. 0309383.8 X-Ray Tube Electron Sources.

Collimation of the X-rays from the source 20 is important to minimize radiation dose to the patient 26. The source 20 therefore includes collimators arranged to restrict X-ray beams to only that part of the patient 26 that lies directly between the source and corresponding detectors. Some suitable collimation systems are disclosed in our co-pending UK patent application No. 0309374.7 entitled X-Ray Sources, and also in UK patent application No. 0216891.2 entitled Radiation Collimation.

To form an image of the patient 26, the patient is placed in position with the part of their body to imaged within the scanning volume 28. Then, with the patient 26 being kept stationary, each of the X-ray source points 22 is operated in turn to scan the patient, and for each source point 22 data from the group of detector elements 16 opposite the source point 22 is used to form an image frame. All of the image frames produced in one scan are then processed to form a three-dimensional tomographic X-ray image of the patient as will be described in more detail below.

Figure 3:
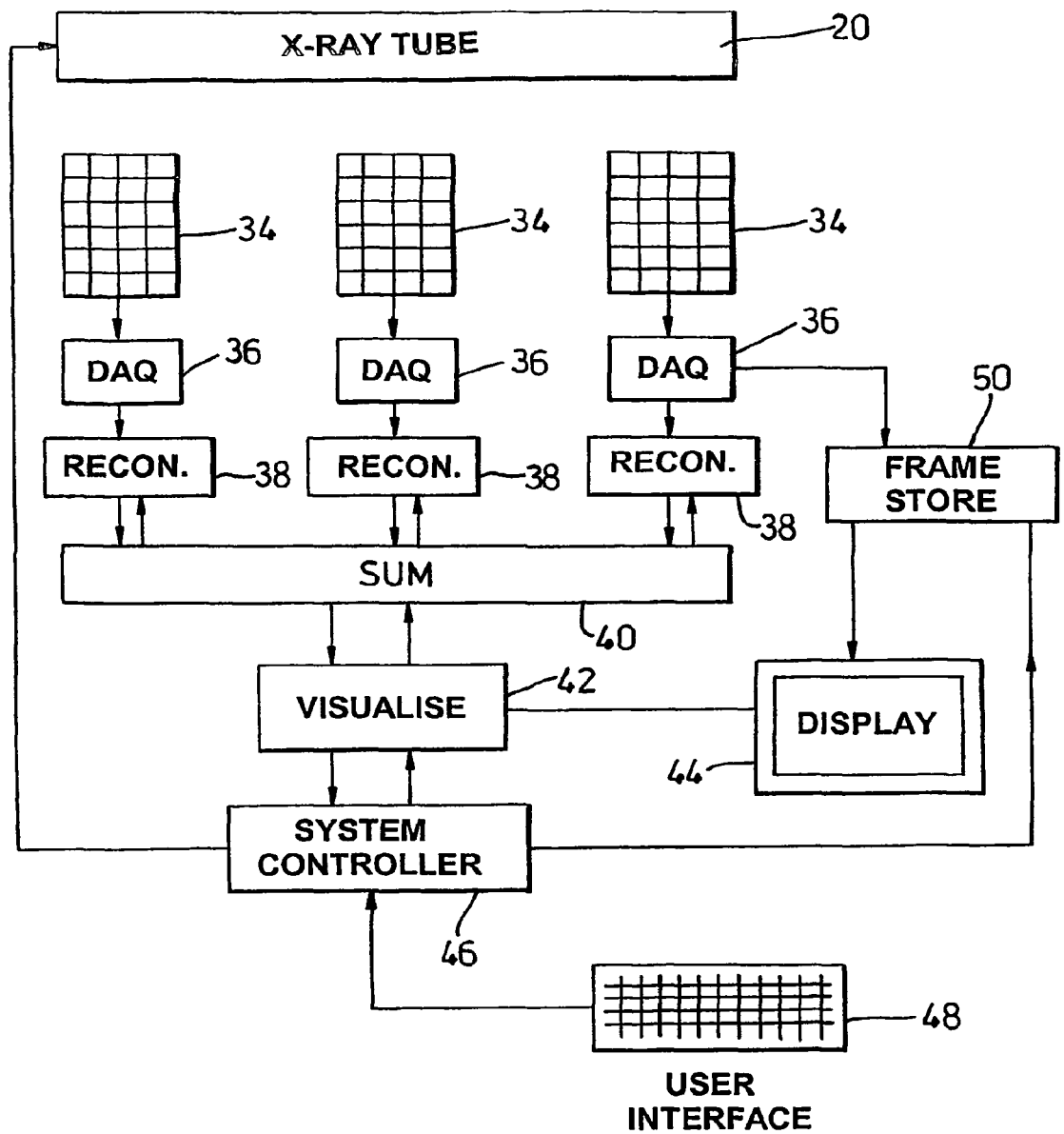
FIG. 3 is a system diagram of a scanner system including the scanner of FIG. 1.

Referring to FIG. 3, the complete X-ray system comprises the multi-focus X-ray tube 22 and detector array 12, which is made up of a number of sensor blocks 34. Each sensor block comprises an array of detecting elements 16, typically 8.times.4 or 16.times.8 pixels, that are electronically coupled to suitable amplifiers, sample-and-hold amplifiers, analogue multiplexor and analogue-to-digital converter. Each sensor block 34 is connected to a respective data acquisition circuit (DAQ) 36 that provides gain and offset correction and, where appropriate, linearization for input to the image reconstruction process. To cope with the high data rates generated by the detector array 12, multiple hardwired image reconstruction circuits 38 are used to process data in parallel from the DAQ circuits 36. The image reconstruction circuits are connected via a summing circuit 40 to visualization circuit 42, which in turn is connected to a display 44. A system controller 46 is connected to, and controls operation of, the X-ray tube 20 and the detector bocks 34 and other circuits 36, 38, 40, 42 and display 44. A user interface 48, which can include, for example, a keyboard, a hand held controller, and action specific control buttons, is connected to the controller 46 to allow a user to control operation of the system.

During each scan the X-ray tube 20 is controlled so that each of the source points 22 produces a beam of X-rays in turn. The order of activation of the source points 22 can be sequential, or can be ordered so as to reduce the thermal load on the tube anode, as described in our co-pending UK patent application No. 0309387.9 entitled X-ray Scanning For each scan, data from each of the detector blocks 34 is processed in the respective DAQ 36 and image reconstruction circuit 38. The reconstructed images from each reconstruction circuit 38 are summed and passed to a visualization unit 42 that creates a 3D tomographic image. The images from subsequent scans are combined to form a real time 3D video image which is shown in the display 44.

For equivalent image quality, the faster the scan time, the higher the X-ray tube current. For example, a 5 ms scan time requires an anode current in excess of 500 mA for high quality medical diagnostic imaging.

It will be appreciated that the combination of a helical trajectory multi-focus X-tray tube 20 and multi-ring X-ray detector 12 with helical slot 24 allows true full volume tomographic image data to be collected with no mechanical movement of X-ray source, X-ray detector or patient. Since no mechanical movement is involved, it is possible to generate volume images very quickly, with the only limitation being the output power of the X-ray tube. The scanner described can therefore provide full three-dimensional X-ray tomographic scans using accurate cone-beam three dimensional reconstruction algorithms over millisecond timescales.

Applications for the scanner in this mode of operation include volume cardiac imaging (single cycle) where movies of cardiac motion can be generated over a single cycle. Assume a cardiac cycle time of 800 ms and a 4 ms tomographic scan time, a single cardiac cycle movie will contain 200 volume tomographic images. A preferred use of this scanner is in cardiac angiography in which iodine contrast agent is passed through the heart and surrounding vessels.

Figure 4:
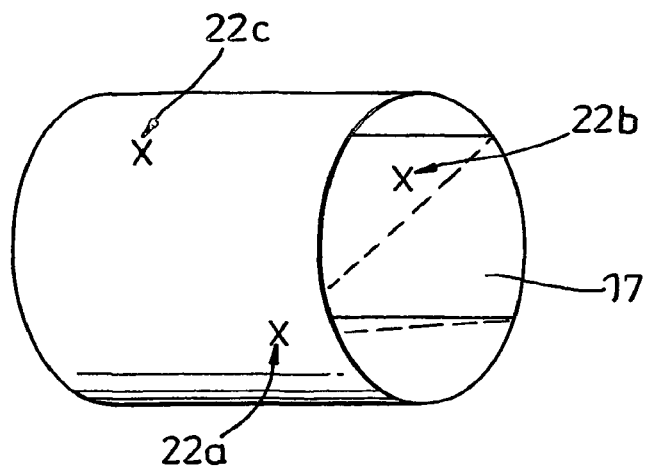
FIG. 4 is a schematic perspective view of the scanner of FIG. 1 reconfigured according to a second embodiment of the invention.

Referring to FIG. 4, in a second mode of operation, the scanner system of FIGS. 1 to 3 is set up for use in fluoroscopy. This can be single plane, bi-plane or multi-plane fluoroscopy. For single plane fluoroscopy a single source point 22a is used, and a beam of X-rays passed from that source point 22a, through the patient, and onto a group 17 of the detector elements 16. The data from the detector elements 16 is used to form an image frame data set which represents a 2 dimensional X-ray projection image of the imaged volume. This process is repeated in successive imaging periods, which may be of the order of 5 ms. It will be appreciated that this is significantly faster than conventional fluoroscopy for which the corresponding period is of the order of 40 ms or more. In this case the image frame data sets are output directly from the DAQs 36 to a frame store 50 from which they can be displayed in turn as images on the display 44 to provide a real time 2D video image of the patient.

Since a large number of X-ray source points 22 are present in the system, it can easily be controlled to alternate between two, three or more source points 22b, 22c spaced around the patient. For each source point 22a 22b, 22c, a corresponding group of detector elements 16 will be used to produce a respective series of fluoroscopic image frames. By cycling between the source points 22a, 22b, 22c simultaneous video images in a number of planes can be produced. These fluoroscopic images can either simply be displayed simultaneously on the display 44 or processed to provide a single video image combining features from each of the plane video images. The angle between planes may be adjusted electronically by switching the location of the emitting electron source. Applications for the system used in this mode are neuroradiology and neuroangiography.

The fluoroscopic images produced can be improved by using the methods described in UK patent application No. 0216893.8 entitled Image Colouring and UK patent application No. 0216889.6 entitled Image Control.

Figure 5:
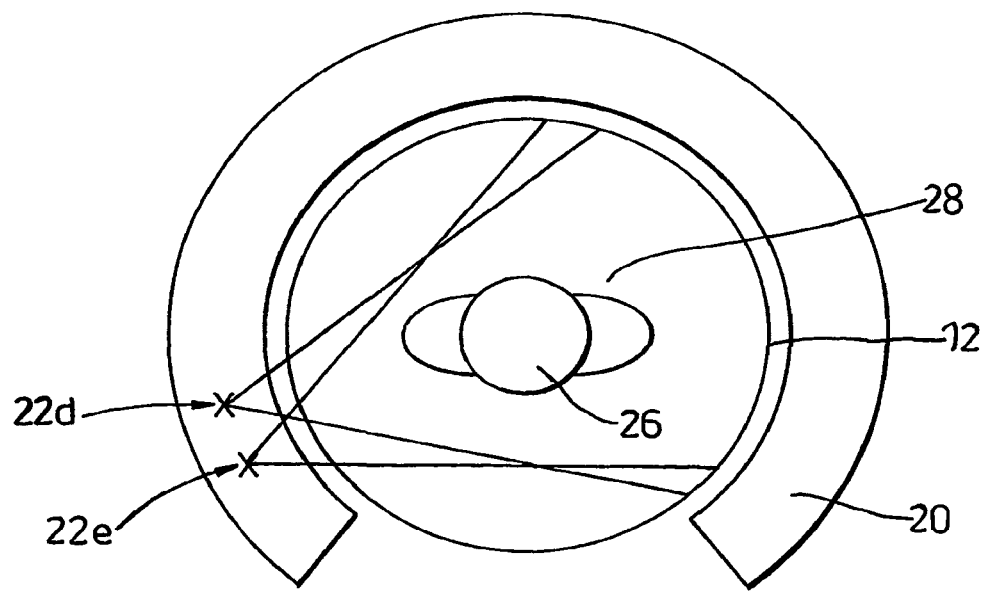
FIG. 5 is a cross section through the scanner of FIG. 1 reconfigured according to a third embodiment of the invention.

Referring to FIG. 5, in a further mode of operation, the system is set up to provide stereo imaging of the imaging volume 28. In this set-up, two source points 22d, 22e are used which are close together. Each of them is activated in turn to produce a respective transmission image data set from a corresponding group of detector elements 16 on the opposite side of the imaging volume 28. These image data sets are stored in the frame store 50. A pair of image frame data sets, one from each source point 22d, 22e, is combined to produce a stereo image data set representing an image of the imaged volume, and successive stereo images can be displayed to produce a real time stereo view video image of the imaged volume 28. The angle between the two sources 22d, 22e, and hence the degree of parallax, can be adjusted dynamically to suit the size of the patient or organ being imaged.

Because the source points 22 to be used, and the order in which they are used, can be controlled by the controller 46 in any suitable order or combination, it is also possible for the scanner to switch rapidly between any of the three modes of operation described above. This will reduce the rate at which data can be collected for each mode, but enables the images produced in each mode to be combined. For example in one mode the scanner is arranged to scan the object repeatedly to produce a 3D tomographic image of the object, but, between each successive pair of scans, to use one of the source points 22 to produce a 2D flouroscopic image of the object. The tomographic image is then analyzed by the visualizing unit 42 to identify specific features, which are then identified with corresponding features on the fluoroscopic image. The fluoroscopic image is then enhanced by mapping features from the 3D image onto the 2D image using software pointers to show the mapped features more clearly. This can be advantageous, for example where one or more features is obscured in the 2D image, or where two or more features cannot be distinguished from each other. Alternatively, features identified in the fluoroscopic image can be mapped directly onto the three-dimensional tomographic image. It will be appreciated that the automatic registration of the fluoroscopic image and volume tomographic data can be of major clinical advantage.

Similar combinations can be made of the stereo view imaging data and the tomographic imaging data, or indeed of all three imaging methods. The combination of volume real-time tomographic imaging, real-time multi-plane fluoroscopy and real-time stereo view imaging in one spatially registered imaging system can lead to shortening of clinical procedures, enhanced diagnosis and, in some cases, a lowering of patient dose.

Figure 6:
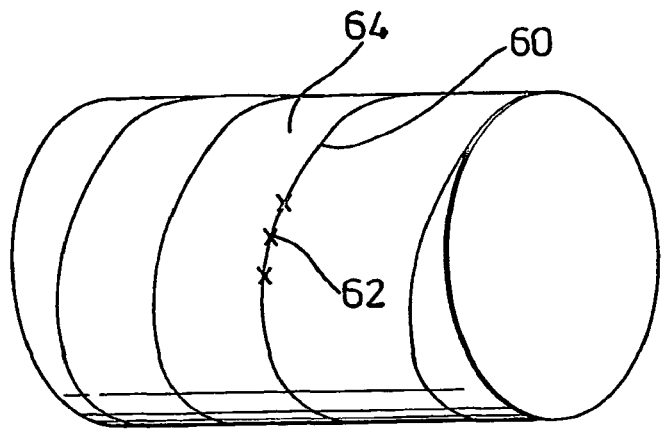
FIG. 6 is a schematic perspective view of an X-ray scanner according to a second embodiment of the invention.
Figure 7:
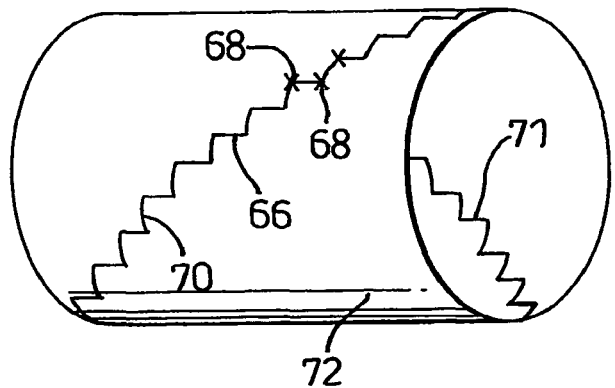
FIG. 7 is a schematic perspective view of an X-ray scanner according to a third embodiment of the invention.
Figure 8:
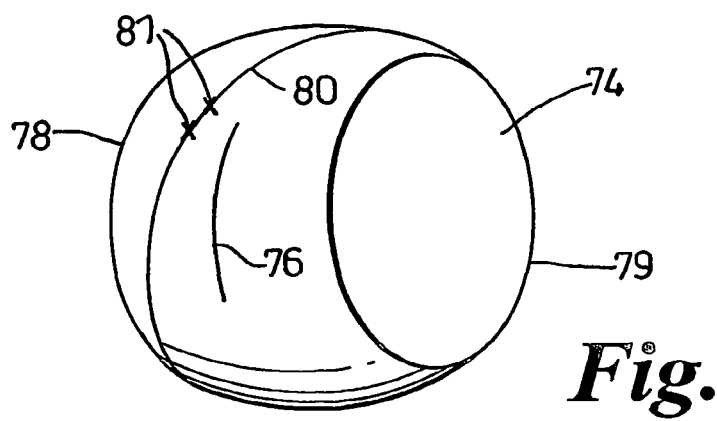
FIG. 8 is a schematic perspective view of an X-ray scanner according to a fourth embodiment of the invention.

It will be appreciated that the exact shape of the X-ray source can be modified substantially. The embodiment described above is the simplest to use in many circumstances as the regular helix with a single turn produces data which is simple to analyze. However, other shapes of source could be used. For example, referring to FIG. 6, in a second embodiment of the invention, a helical locus 60 of X-ray source points 62 is again used, but in this case the helix has a plurality of turns around the detector array 64. Referring to FIG. 7, in a fourth embodiment, the locus 66 of source points 68 is not in a helix, but is made up of two stepped loci 70, 71 each extending half way round the circumference of the cylindrical detector array 72 and along its full length. Finally, referring to FIG. 8, in a fourth embodiment the detector array 74 is not straight cylindrical, but instead is part spherical being of larger circumference at its centre line 76 than at its longitudinal ends 78, 79. The locus 80 of source points 81 extends from one end 78 of the detector array 74 to the other 79 while following a single turn around its circumference.

I claim:

1. A method of operating an X-ray imaging system in a first mode and in a second mode, said X-ray imaging system comprising a scanning volume within which an object being scanned is positioned, a detector array surrounding a portion of the scanning volume, and an X-ray source positioned around an exterior of the detector array, wherein the X-ray source comprises an anode with a plurality of source points, and wherein said object, said detector array and said X-ray source are stationary during operation, the method comprising:

in said first mode:
sequentially operating X-ray source points of said plurality of source points to scan the object;
using a detector element positioned across the scanning volume and opposite the operated X-ray source point for detecting X-rays transmitted through the object being scanned;
forming first images from each of said operated X-ray source points using transmission data from the detector element opposite said source point; and
processing the first images to form a three-dimensional tomographic X-ray image;
in said second mode:
operating an X-ray source point;
using a detector element positioned across the scanning volume and opposite the operated X-ray source point for detecting X-rays transmitted through the object being scanned; and
forming second images from each of said operated X-ray source points using transmission data from said detector element opposite said source points, wherein each of said second images represents a two-dimensional X-ray projection image of the scanned volume.

2. The method of claim 1, wherein the X-ray imaging system further comprises a controller to separately activate each of the plurality of source points.

3. The method of claim 2, wherein the controller is used to switch the X-ray imaging system from the first mode to the second mode and from the second mode to the first mode.

4. The method of claim 1, wherein one of said plurality of source points is operated in the second mode to produce a single plane fluoroscopic image.

5. The method of claim 1, wherein two of said plurality of source points are operated in the second mode to produce a bi-plane fluoroscopic image.

6. The method of claim 1, wherein more than two source points of said plurality of source points are operated in the second mode to produce a multi-plane fluoroscopic image.

7. The method of claim 6, wherein the more than two source points of said plurality of source points are operated in a cyclical manner.

8. The method of claim 6, wherein an angle between planes of the multi-plane fluoroscopic image is adjusted by changing the more than two source points of said plurality of source points.

9. The method of claim 1, wherein said method in the second mode is repeated in successive imaging periods to produce a real time two-dimensional video image.

10. The method of claim 9, wherein one of said successive imaging periods is on the order of 5 ms.

11. The method of claim 1, wherein said method in the first mode is repeated in successive scans.

12. The method of claim 11, wherein images generated from said successive scans are combined to form a real time three-dimensional video image.

13. The method of claim 1, further comprising outputting the first images to a frame store memory for display.

14. The method of claim 1, further comprising outputting the second images to a frame store memory for display.

* * * * *